United States Patent [19]

Kijima et al.

[11] 4,130,659
[45] Dec. 19, 1978

[54] POLYPRENYL CARBOXYLIC ACID COMPOUND AND HYPOTENSIVE AGENT CONTAINING IT AS ACTIVE INGREDIENT

[75] Inventors: Shizumasa Kijima, Tokyo; Toshiji Igarashi, Tokorozawa; Isao Yamatsu, Tokyo; Kimio Hamamura, Kashiwa; Yoshikage Nakajima, Tokyo; Norio Minami, Kawasaki; Youji Yamagishi; Yuithi Inai, both of Tokyo, all of Japan

[73] Assignee: Eisai Co., Ltd., Tokyo, Japan

[21] Appl. No.: 903,395

[22] Filed: May 8, 1978

Related U.S. Application Data

[62] Division of Ser. No. 796,693, May 13, 1977, Pat. No. 4,107,193.

[30] Foreign Application Priority Data

May 27, 1976 [JP] Japan .................................. 51-60583

[51] Int. Cl.$^2$ ..................... A61K 31/23; A61K 31/20
[52] U.S. Cl. .................................... 424/312; 424/318
[58] Field of Search ......................................... 424/312

[56] References Cited

U.S. PATENT DOCUMENTS 3,939,202  2/1976  Matsui et al. ..................... 260/410

Primary Examiner—Allen J. Robinson
Attorney, Agent, or Firm—Blanchard, Flynn, Thiel, Boutell & Tanis

[57] ABSTRACT

A polyprenyl carboxylic acid compound represented by the following general formula:

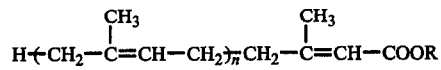

wherein R stands for a hydrogen atom or an alkyl, alkenyl, cycloalkyl or aryl group, and n is an integer of 6 to 11. This compound is effective to treat hypertension of warm blooded animals.

10 Claims, 1 Drawing Figure

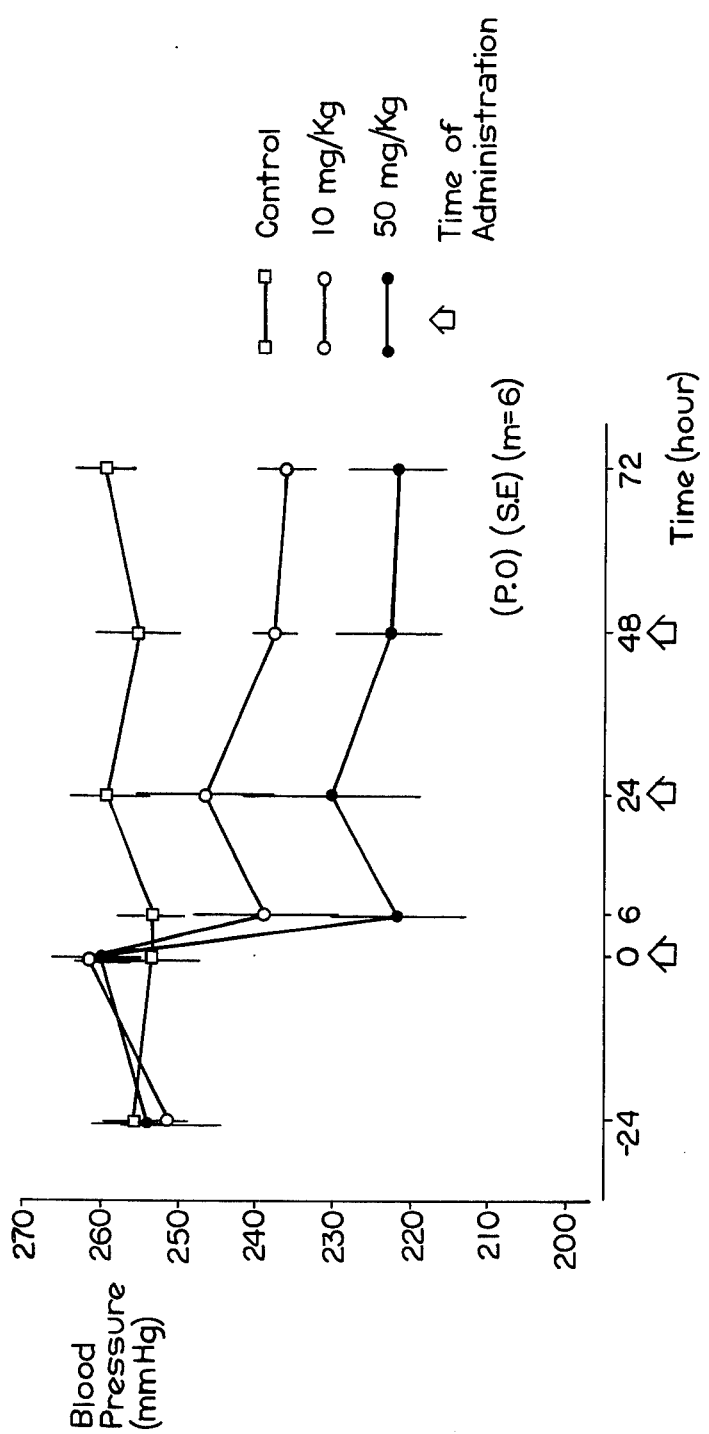

POLYPRENYL CARBOXYLIC ACID COMPOUND AND HYPOTENSIVE AGENT CONTAINING IT AS ACTIVE INGREDIENT

This is a division, of application Ser. No. 796,693 filed May 13, 1977, now U.S. Pat. No. 4,107,193.

BACKGROUND OF THE INVENTION

1. Field of the Invention

The present invention relates to polyprenyl carboxylic acid compounds represented by the following general formula (I):

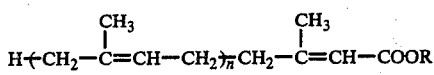  (I)

wherein R stands for a hydrogen atom or an alkyl, alkenyl, cycloalkyl or aryl group, and n is an integer of 6 to 11, and to a hypertensive agent comprising as an active ingredient there polyprenyl carboxylic acid compounds.

SUMMARY OF THE INVENTION

This novel polyprenyl carboxylic acid compound can be obtained, for example, by reacting a polyprenyl methyl ketone represented by the following chemical formula (II):

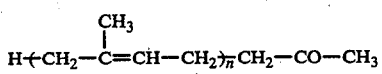  (II)

wherein n is as defined above,
with a Wittig reagent derived from an αhalogenoacetic acid compound represented by the followng general formula (III):

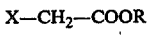  (III)

wherein X stands for a halogen atom and R is as defined above.

The polyprenyl methyl ketone (II) that is used in the present invention, for example, solanesyl methyl ketone (n = 9) is obtained by brominating 3,7,11,15,19,23,27,31-octamethyl-dotriacontaoctane-1,6,10,14,18,22,26,30-ol-6 obtained by purely synthetic chain extension of isoprene units (see, for example, Japanese Patent Publication No. 17514/64) or solanesol, followed by condensation with an acetoacetic acid ester. It can also be obtained by brominating natural solanesol derived from tobacco or potato leaves by extraction and purification by R. L. Rowland, et al. [J. Am. Chem. Soc., 78, p. 4680 (1956)], J. D. Grossman, et al. [Nature, 199, p. 661 (1963)] and Toyoda, et al. [Journal of Japanese Society of Agricultural Chemistry, 44, p. 257 (1970)], followed by condensation with an acetoacetic acid ester. As the Wittig reagent derived from an αhalogenoacetic compound represented by the general formula (III), that is used in the present invention, there can be mentioned those derived from α-halogenoacetic acid compounds and phosphorus compounds such as triphenyl phosphine [$(C_6H_5)_3P$], phenyldialkoxy phosphines [$C_6H_5(AlkO)_2P$] and trialkyl phosphites [$P(OAlk)_3$] (in the above formulae, Alk stands for a lower alkyl group having 1 to 5 carbon atoms) or 1-substituted-methyl-triphenyl phosphonium salts [$(C_6H_5)_3P^+.CH_2COOR.X^-$], 1-substituted-methylalkylphenyl phosphinates [$C_6H_5.(AlkO).P(O).CH_2COOR$] and 1-substituted-methyl-dialkyl phosphonates [$(AlkO)_2.P(O).CH_2COOR$] prepared according to methods taught by Wordworth, et al. [J. Am. Chem. Soc., 83, p. 1733 (1961)], Horner, et al. [Ber., 95, p. 581 (1962)] and Greenwald, et al. [J. Org. Chem., 28, 1128 (1963)]. The reaction between the polyprenyl methyl ketone (II) and the Wittig reagent derived from the α-halogenoacetic acid compound (III) can be carried out according to a customary Wittig reaction (see literature references mentioned above).

In general, an alkaline agent such as butyl lithium, sodium amide, sodium hydride, sodium methylate, potassium t-butoxide, potassium hydroxide, sodium carbonate, trialkyl amine or the like is added in conducting the reaction. The reaction may be advanced in the absence of a solvent, but when a solvent customarily used for the Wittig reaction, such as benzene, toluene, xylene, hexane, petroleum ether, ligroin, cyclohexane, ethyl ether, isopropyl ether, dioxane, tetrahydrofuran, ethyl acetate, dimethyl formamide or the like, is used for the reaction, the reaction can be advanced more smoothly and the post treatment can be facilitated.

The "R" in the general formula of polyprenyl carboxylic acid compound stands for hydrogen, or an alkyl, alkenyl, cycloalkyl or aryl group. The alkyl and alkenyl are preferred to have one to five carbon atoms and the cycloalkyl group is preferred to have 6 carbon atoms; the aryl is preferred to be phenyl. The alpha-halogenoacetic acid compound to be used for preparation of Wittig reagents is preferred to contain chlorine, bromine or iodine as "X".

The compound (I) formed according to the above-mentioned process of the present invention includes steric isomers, a cis-form isomer and a trans-form isomer, but they can be separated easily by adsorption chromatography.

For example, when 30 g of 1-ethoxycarbonyl-2,6,10,14,18,22,26,30,34,38-decamethyl-nonatriacontadecaene-1,5,9,13,17,21,25,29,33,37 (n = 9, R = $C_2H_5$, trans-form content = 77%), which is included in the intended compound of the present invention, is subjected to adsorption chromatography using 3 Kg of silica gel in benzene, the cis-form is first eluted and then, the trans-form is eluted to obtain 17.2 g of 1-ethoxycarbonyl-2,6,10,14,18,22,26,30,34,38-decamethyl-nonatriacontadecaene-1,5,9,13,17,21,25,29,33,37 having a trans-form content of 98% (the trans-form yield being 73%).

Alkali metal salts, alkaline earth metal salts, ammonium salts, trimethyl amine salts, dicyclohexyl amine salts, acid anhydrides and the like of compounds (I) of the present invention where R stands for a hydrogen atom are included in the intended compound of the present invention.

Various hypertensive agents have heretofore been used for treatment of hypertension. However, these hypertensive agents show various side effects, and large quantity administration or long-time continuous administration of these hypertensive agents involves problems. For example, diuretic hypertensive agents represented by sulfonamide type agents and thiazide derivatives show serious side effects causing uratemia and hypo-kalemia, sympatholytic agents represented by reserpine derivatives and methyldopa agents cause thirst, clouding of consciousness and orthostatic hypertensive asthenia as side effects, and vasodilators such as apresoline agents cause headache, tachycardia and angina pectoris as side effects. We made research works with a view to developing hypertensive agents that cause none of such side effects, and as a result, we found compounds (I) of the present invention.

BRIEF DESCRIPTION OF THE DRAWING

The drawing illustrates the antihypertensive activity of 1-ethoxycarbonyl-2,6,10,14,18,22,26,30,34,38-decamethyl-nonatriacontadecaene-1,5,9,13,17,21,25,29,33,37 (compound A) of the present invention when administered to spontaneous hypertensive rats. The mark "□" indicates the control, "o" indicates administration of 10 kg/Kg of the compound A and "●" indicates administration of 50 mg/Kg of the compound A.

The pharmacological activity and toxicity (acute toxicity) of compounds of the present invention revealed by animal experiments are as follows.

Pharmacological Tests

Antihypertensive activity in the spontaneous hypertensive rats of Okamoto and Aoki (hereinafter referred to as "SHR"):

Method

The antihypertensive activity of the test compound was determined in SHR of 10 weeks age. The systolic blood pressure was about 250 mmHg. The blood pressure was measured by a tail cuff method using a continuous systolic pressure monitor (SCS-301, Shimazu Seisakusho K.K.).

The test compound was suspended in gum arabic solution. The test animals were divided into three groups which consisted of 6 animals, respectively.

To the animals in two groups either 10 or 50 mg/kg of the test compound was orally administered once a day for three consecutive days. The animals in the other group were treated with gum arabic solution and served as the control group.

Test Compound

1-Ethoxycarbonyl-2,6,10,14,18,22,26,30,34,38-decamethylnonatriacontadecaene-1,5,9,13,17,21,25,29,33,37 (hereinafter referred to as "Compound A").

Result

In the group of SHR treated with Compound A for 3 days at a daily dose of 10 or 50 mg/kg, the blood pressure was definitely reduced, whereas the blood pressure in the control group remained unchanged at a mean level of 253 mmHg, as shown in FIG. 1.

The level of blood pressure was reduced to 239 or 222 mmHg 6 hours after the first administration of 10 or 50 mg/kg of Compound A. The reduced blood pressure under the effect of Compound A remained at the lowered level even 24 hours after the administration 10 or 50 mg/kg of Compound A. These facts indicate that the hypertensive effect of Compound A is long lasting.

Toxicological Test: acute toxicity

Method

Sprague Dawley rats of 7 weeks age, male and female, were used. Compound A was orally administered in the form of a gum arabic suspension. Body weight, food consumption and behavior-change of test animals were investigated for 7 days after the administration of Compound A.

Result

Neither weight gain nor food consumption was influenced by the administration of Compound A. None of 10 male and 10 female rats which were given 10 g/Kg of Compound A died and showed toxic behavior changes.

Consideration on the results of pharmacological and toxicological tests

It was suggested that the antihypertensive activity of Compound A is relatively moderate but long lasting. It seems remarkable that Compound A showed antihypertensive activity in the tests which was carried out on SHR, because this animal is considered to be the most suitable experimental model for essential hypertension in humam beings in the aspects of the etiology of hypertension and the reactions of this animal to hypertensive drugs. From the results of the acute toxicity tests, the Compound A seems to be of low toxicity.

According to the above-mentioned results of pharmacological and toxicological tests, the compound (I) of the invention represented by Compound A seems to be a desirable hypertensive agent, especially its long lasting effect and low toxicity. Therefore, the compound (I) of the present invention is expected to be effective for prevention and treatment of renal hypertension, nervous hypertension, essential hypertension and other hypertensive diseases. The administration and dosage of compound (I) of the present invention can be appropriately chosen and adjusted depending on the disease condition and the like. In the case of oral administration to adults, in general, it is preferred that the compound (I) of the present invention be administered in an amount of 10 to 200 mg, especially 50 to 100 mg, per day.

The compound (I) of the present invention can be formed into medicinal preparations according to customary techniques.

Accordingly, the present invention includes a medicinal composition suitable for the medical treatment of human beings which comprises at least one member selected from compounds represented by the above general formula (I) and their pharmaceutically acceptable salts. This composition is administered together with an optional pharmaceutical carrier or excipient according to a customary method.

It is preferred that this composition be administered in the form and state suitable for absorption from the stomach and intestines. For example, unit dosage tablets and capsules for oral administration may comprise binders such as syrup, gum arabic, gelatin, sorbitol, tragacanth gum and polyvinyl pyrrolidone, excipients such as lactose, sugar, corn starch, calcium phosphate, sorbitol and glycine, lubricants such as magnesium stearate, talc, polyethylene glycol and silica, disintegrating agents such as potato starch, acceptable wetting agents such as sodium lauryl sulfate, and other customary diluents. Further, tablets may be coated according to methods known in the art. Liquid preparations for oral administration may be aqueous or oily suspensions, solutions, syrups, elixirs and the like. Further, they may be dry products to be redissolved in water or other suitable vehicle before administration. These liquid preparations may comprise customary additives, for example, suspending agents such as sorbitol syrup, methyl cellulose, glucose/sugar syrup, gelatin, hydroxyethyl cellulose, carboxymethyl cellulose, aluminum stearate gel and hydrogenated edible fat, emulsifiers such as lecithin, sorbitol mono-oleate and gum arabic, non-aqueous vehicles such as almond oil, fractionated coconut oil, oily esters, propylene glycol and ethyl alcohol, and antiseptics such as methyl p-hydroxybenzoate, propyl p-hydroxybenzoate and sorbic acid.

Compositions for injection are provided in the form of unit dose ampules or large quality vessels together with an antiseptic. Injection compositions may be suspensions, solutions and emulsions in oily and aqueous vehicles. They may include such adjuvants as suspending agents, stabilizers and dispersants. The active ingredient may be a powder to be re-dissolved in a suitable vehicle, for example, sterilized water, before application.

The present invention will now be described by reference to the following Examples.

EXAMPLE 1

1-Ethoxycarbonyl-2,6,10,14,18,22,26-heptamethyl-heptacosaheptaene-1,5,9,13,17,21,25

(a) Synthesis

Powdery sodium ethylate obtained from 4.5 g of metallic sodium and 100 ml of ethanol was suspended in 200 ml of n-hexane, and 45 g of triethyl phosphonoacetate was added dropwise to the suspension below 10° C. under agitation. Agitation was continued for 20 minutes, and 47 g of wholly trans-form 6,10,14,18,22,26-hexamethyl-heptacosahexaene-5,9,13,17,21,25-one-2 (hexaprenyl methyl ketone or farnesylfarnesyl methyl ketone) was added to the mixture below 10° C. under agitation. Reaction was conducted at the same temperature for 2 hours, and water was added to the reaction mixture and the n-hexane layer was separated. The n-hexane layer was washed with water and dried with Glauber's salt. Distillation of the solvent gave 52 g of 1-ethoxycarbonyl-2,6,10,14,18,26-heptamethylheptacosaheptaene-1,5,9,13,17,21,25.

Yield 96.2%

Elementary Analysis Value as $C_{37}H_{60}O_2$: Calculated: C = 82.75%, H = 11.29% Found: C = 82.77%, H = 11.27%

(b) Measurement of Ratio of Cis-Form Content and Trans-Form Content

The product (10 g) was spotted on a thin layer [Kiesel Gel 60F254 manufactured by Merck Co. (20 cm × 20 cm, 0.25 mm thick)] and was developed along 15 cm by using 5% isopropyl ether/n-hexane mixed solvent as a developing solvent. Measurement was conducted by using a densitometer (Chromatoscanner CS-900 manufactured by Shimazu Seisakusho K.K.) according to the reflection UV method adopting λ max 410 mμ as a reference wave length and ε max 230 m∞ as a sample wave length. Linear scanning was used as the scanning, and the slit was 9.3 in height and 0.5 mm in width.

As a result of the measurement, it was found that the cis-form/trans-form content ratio was 17/83.

(c) Various Spectral Observations

The molecular weight (M+ 536) was confirmed from the mass spectrum. A carbonyl stretching vibration was observed at 1710 cm$^{-1}$ in the infrared spectrum. In the NMR spectrum, an absorption owing to the ethyl group was newly observed.

(d) Separation of Cis-Form and Trans-Form

In 150 ml of n-hexane was dissolved 50 g of 1-ethoxycarbonyl-2,6,10,14,18,26-heptamethyl-heptacosaheptaene-1,5,9,13,17,21,25 obtained in (a) above, and adsorption chromatography was carried out by using a glass column (11 cm in diameter and 80 cm in height) filled with 3 Kg of silica gel in n-hexane. Developing solvents were passed through the column by SV1. First, 1 l of hexane was passed, and then, 0.5 l of 10% benzene/n-hexane, 0.5 l of 20% benzene/n-hexane, 0.5 l of 30% benzene/n-hexane and 20 l of 50% benzene/n-hexane were passed in succession. Then, 3 l of 50% benzene/n-hexane was passed to elute 2.8 g of the cis-form alone, 18.1 g of a mixture of the cis-form and trans-form was then eluted by 10 l of 50% benzene/n-hexane, and then, 29 g of the trans-form alone was obtained by 8 l of 50% benzene/n-hexane and 12 l of benzene.

EXAMPLE 2

1-Ethoxycarbonyl-2,6,10,14,18,22,26,30-octamethyl-hentriacontaoctaene-5,9,13,17,21,25,29

(a) Synthesis:

In the same manner as described in (a) of Example 1, 45 g of triethyl phosphonoacetate and 54 g of wholly trans-form 6,10,14,18,22,26,30-heptamethyl-hentriacontaheptaene-5,9,13,17,21,25,29-one-2 (ordinarily called farnesylgeranyl methyl ketone) were reacted and treated to obtain 59.3 g of the intended compound.

Yield:

97.1%

Elementary Analysis Values as $C_{42}H_{68}O_2$: Calculated: C = 83.41%, H = 11.27% Found: C = 83.38%, H = 11.33%

(b) Measurement of Ratio of Cis-Form Content and Trans-Form Content:

In the same manner as described in (b) of Example 1, the cis-form/trans-form content ratio in the product was measured. As a result, it was found that the cis-form/trans-form content ratio was 18/82.

(c) Various Spectral Observations

The molecular weight (M+ 604) was confirmed from the mass spectrum. In the infrared spectrum, a carbonyl stretching vibration was observed at 1,710 cm$^{-1}$.

In the NMR spectrum, an absorption owing to an ethyl group was newly observed.

(d) Separation of Cis-Form and Trans-Form

In the same manner as described in (d) of Example 1, 28 g of the product obtained in (a) above was treated to effect separation of the cis-form and trans-form, whereby 1.4 g of the cis-form and 18.2 g of the trans-form were obtained. The obtained trans-form isomer was solidified when stored in a refrigerator and the solid had a melting point of 15° C.

EXAMPLE 3

1-Ethoxycarbonyl-2,6,10,14,18,22,26,30,34-nonamethylpentatriacontanonaene-1,5,9,13,17,21,25,29,33.

(a) Synthesis

In the same manner as described in (a) of Example 1, 23 g of triethyl phosphonoacetate and 30 g of wholly trans-form 6,10,14,18,22,26,30,34-octamethyl-pentatriacontaoctaene-5,9,13,17,21,25,29,33-one-2 (ordinarily called farnesyl-farnesylgeranyl methyl ketone) were reacted and treated to obtain 32.7 g of the intended compound.

Yield 97.6%

Elementary Analysis Values as $C_{47}H_{76}O_2$: Calculated: C = 83.75%, H = 11.43% Found: C = 83.86%, H = 11.38%

(b) Measurement of Ratio of Cis-Form Content and Trans-Form Content cis-form/trans-form content ratio = 18/82

(c) Various Spectral Observations:

Mass spectrum: $M^+$ 672
Infrared spectrum: $\nu$ C=O 1710 cm$^{-1}$
NMR spectrum: absorption owing to an ethyl group newly appeared

EXAMPLE 4

1-Methoxycarbonyl-2,6,10,14,18,22,26,30,34,38-decamethyl-nonatriacontadecaene-1,5,9,13,17,21,25,29,33,37

(a) Synthesis

A mixture of 20.0 g of carbomethoxymethylenetriphenylphosphorane and 2.0 g of solanesyl methyl ketone was agitated at a temperature of 160° to 170° C. for 20 hours. After cooling, 30 ml of benzene was added to the reaction mixture and the solution was washed with water. The mixture was dried with sodium sulfate. Distillation of the solvent gave 21.3 g of 1-methoxycarbonyl-2,6,10,14,18,22,26,30,34,38-decamethyl-nonatriacontadecaene-1,5,9,13,17,21,25,29,33,37.

Elementary Analysis Values as $C_{51}H_{82}O_2$: Calculated: C = 84.23%, H = 11.37% Found: C = 84.36%, H = 11.33%

(b) Measurement of Ratio of Cis-Form Content and Trans-Form Content:

cis-form/trans-form content ratio = 40/60

(c) Various Spectral Observations:

Mass spectrum: $M^+$ 727
Infrared spectrum: $\nu$ C=O 1710 cm$^{-1}$
NMR spectrum: absorption owing to a methyl group newly appeared.

EXAMPLE 5

1-Ethoxycarbonyl-2,6,10,14,18,22,26,30,34,38-decamethyl-nonatriacontadecaene-1,5,9,13,17,21,25,29,33,37

(a) Synthesis

In 50 ml of benzene was suspended 1.9 g of sodium ethylate, and 6.3 g of triethyl phosphonoacetate was added dropwise to the suspension at 20° C. under agitation over a period of 10 minutes. Agitation was further continued for 20 minutes. Then, 13.4 g of solanesyl methyl ketone was added to the mixture at 20° C. under agitation, and agitation was conducted at the same temperature for 5 hours. Water was added to the reaction mixture, and the benzene layer was separated and dried with sodium sulfate. Distillation of the solvent gave 14.5 g of 1-ethoxycarbonyl-2,6,10,14,18,22,26,30,34,38-decamethyl-nonatriacontadecaene-1,5,9,13,17,21,25,29,33,37. The yield was 98.0%. In the thin layer of the so obtained carboxylic acid ester, the spot of the starting compound disappeared completely.

(b) Measurement of Ratio of Cis-Form Content and Trans-Form Content cis-form/trans-form content ratio = 18/82

(c) Various Spectral Observations

Mass spectrum: $M^+$ 740
Infrared spectrum: $\nu$ C=O 1710 cm$^{-1}$
NMR spectrum: absorption owing to an ethyl group newly appeared.

EXAMPLES 6 to 10

1-Ethoxycarbonyl-2,6,10,14,18,22,26,30,34,38-decamethyl-nonatriacontadecaene-1,5,9,13,17,21,25,29,33,37

In the same manner as described in Example 1, triethyl phosphonoacetate and solanesyl methyl ketone were reacted and treated in the absence of a solvent or by using a solvent indicated below to obtain results shown in the following Table.

Table

| Example No. | Solvent | Reaction Temperature (°C) | Reaction Time (hours) | Yield (%) | Trans-Form Content (%) |
|---|---|---|---|---|---|
| 6 | dimethyl formamide | 60 | 7 | 97.2 | 76 |
| 7 | not used | 50 | 5 | 95.5 | 77 |
| 8 | dioxane | 20 | 6 | 93.7 | 78 |
| 9 | tetrahydrofuran | 20 | 5 | 96.7 | 78 |
| 10 | ethyl acetate | 25 | 5 | 96.8 | 79 |

The measurement of the trans-form and cis-form contents was carried out in the same manner as described in (b) of Example 1. Various spectra were observed in the same manner as described in (c) of Example 1.

EXAMPLE 11

1-t-Butoxycarbonyl-2,6,10,14,18,22,26,30,34,38-decamethyl-nonatriacontadecaene-1,5,9,13,17,21,25,29,33,37

(a) Synthesis

In 50 ml of n-hexane was suspended 1.0 g of sodium ethylate, and 3.8 g of t-butyl diethylphosphonoacetate was added dropwise to the suspension under agitation at 15° to 20° C. Then, 6.7 g of solanesyl methyl ketone was added to the mixture. Then, the reaction and post treatment were carried out in the same manner as described in (a) of Example 1 to obtain 7.4 g of 1-t-butoxycarbonyl-2,6,10,14,18,22,26,30,34,38-decamethyl-nonatriacontadecaene-1,5,9,13,17,21,25,29,33,37.

Yield 96.4%

Elementary Analysis Values as $C_{54}H_{88}O_2$: Calculated: C = 84.31%, H = 11.53% Found: C = 84.20%, H = 11.61%

(b) Measurement of Ratio of Cis-Form Content and Trans-Form Content cis-form/trans-form content ratio = 19/81

(c) Various Spectral Observations

Mass spectrum: $M^+$ 768
Infrared spectrum: $\nu$ C=O 1710 cm$^{-1}$
NMR spectrum: absorption owing to a t-butyl group newly appeared.

EXAMPLE 12

1-Cyclohexyloxycarbonyl-2,6,10,14,18,22,26,30,34,38-decamethyl-nonatriacontadecaene-1,5,9,13,17,21,25,29,33,37

(a) Synthesis

In the same manner as described in (a) of Example 1, 4.2 g of cyclohexyl diethylphosphonoacetate and 4.2 g of solanesyl methyl ketone were reacted and treated to obtain 7.4 g of 1-cyclohexyloxycarbonyl-2,6,10,14,18,22,26,30,34,38-decamethyl-nonatriacontadecaene-1,5,9,13,17,21,25,29,33,37.

Yield 94.4%
Elementary Analysis Values as $C_{56}H_{90}O_2$: Calculated: C = 84.57%, H = 11.41% Found: C = 84.64%, H = 11.38%

(b) Measurement of Ratio of Cis-Form Content and Trans-Form Content cis-form/trans-form content ratio = 41/59

(c) Various Spectral Observations:

Mass spectrum: $M^+$ 784
Infrared spectrum: $\nu$ C=O 1710 cm$^{-1}$
NMR spectrum: absorption owing to a cyclohexyl group newly appeared.

EXAMPLE 13

1-n-Butoxycarbonyl-2,6,10,14,18,22,26,30,34,38-decamethyl-nonatriacontadecaene-1,5,9,13,17,21,25,29,33,37

(a) Synthesis

In the same manner as described in (a) of Example 1, 7.6 g of n-butyl diethylphosphonoacetate and 6.7 g of solanesyl methyl ketone were reacted and treated to obtain 14.7 g of 1-n-butoxycarbonyl-2,6,10,14,18,22,26,30,34,38-decamethyl-nonatriacontadecaene-1,5,9,13,17,21,25,29,33,37.

Yield 95.5%
Elementary Analysis Values as $C_{54}H_{88}O_2$: Calculated: C = 84.31%, H = 11.53% Found: C = 84.07%, H = 11.59%

(b) Measurement of Ratio of Cis-Form Content and Trans-Form Content cis-form/trans-form content ratio = 17/83

(c) Various Spectral Observations:

Mass spectrum: $M^+$ 770
Infrared spectrum: $\nu$ C=O 1710 cm$^{-1}$
NMR spectrum: absorption owing to an n-butyl group newly appeared.

EXAMPLE 14

1-Vinyloxycarbonyl-2,6,10,14,18,22,26,30,34,38-decamethyl-nonatriacontadecaene-1,5,9,13,17,21,25,29,33,37

(a) Synthesis

In the same manner as described in (a) of Example 1, 7.0 g of vinyl diethylphosphonoacetate and 6.7 g of solanesyl methyl ketone were reacted and treated to obtain 14.5 g of 1-vinyloxycarbonyl-2,6,10,14,18,22,26,30,34,38-decamethyl-nonatriacontadecaene-1,5,9,13,17,21,25,29,33,37.

Yield 98.1%
Elementary Analysis Values as $C_{52}H_{82}O_2$: Calculated: C = 84.49%, H = 11.18% Found: C = 84.31%, H = 11.25%

(b) Measurement of Ratio of Cis-Form Content and Trans-Form Content cis-form/trans-form content ratio = 17/83

(c) Various Spectral Observations

Mass spectrum: $M^+$ 739
Infrared spectrum: $\nu$ C=O 1710 cm$^{-1}$
NMR spectrum: absorption owing to a vinyl group newly appeared.

EXAMPLE 15

1-Phenoxycarbonyl-2,6,10,14,18,22,26,30,34,38-decamethyl-nonatriacontadecaene-1,5,9,13,17,21,25,29,33,37.

(a) Synthesis

In the same manner as described in (a) of Example 1, 8.2 g of diethyl phenylphosphonoacetate and 6.7 g of solanesyl methyl ketone were reacted and treated to obtain 14.8 g of 1-phenoxycarbonyl-2,6,10,14,18,22,26,30,34,38-decamethyl-nonatriacontadecaene-1,5,9,13,17,21,25,29,33,37.

Yield 93.8%
Elementary Analysis Values as $C_{56}H_{84}O_2$: Calculated: C = 85.22%, H = 10.73% Found: C = 85.18%, H = 10.79%

(b) Measurement of Ratio of Cis-Form Content and Trans-Form Content cis-form/trans-form content ratio = 16/84

(c) Various Spectral Observations

Mass spectrum: $M^+$ 789
Infrared spectrum: $\nu$ C=O 1710 cm$^{-1}$
NMR spectrum: absorption owing to a phenyl group newly appeared.

EXAMPLE 16

1-Ethoxycarbonyl-2,6,10,14,18,22,26,30,34,38,42-undecamethyl-tritetracontaundecaene-1,5,9,13,17,21,25,29,33,37,41

(a) Synthesis

In the same manner as described in (a) of Example 1, 21.3 g of triethyl phosphonoacetate and 50 g of 6,10,14,18,22,26,30,34,38,42-decamethyl-tritetraconta-decaene-5,9,13,17,21,25,29,33,37,41-one-2 (ordinarily called farnesylfarnesylgeranylgeranyl methyl ketone were reacted and treated to obtain the intended compound.

In 6,10,14,18,22,26,30,34,38,40-decamethyl-tritetracontadecaene-5,9,13,17,21,25,29,33,37,41-one-2 used in the above reaction, the trans-form content was 82% with respect to the double bond at the 5-position nearest the carbonyl group, but all of other linkages were wholly of the trans-form. It was a white crystal having a melting point of 39° to 40° C. In 100 ml of n-hexane was dissolved 54.8 g of the resulting product, and purification was carried out by using a glass column packed with 1 Kg of silica gel in n-hexane according to adsorption chromatography (20% benzene/n-hexane mixed solvent was used as an eluting solvent) to obtain 51.5 g of a pure product of the intended compound.

Yield 94.1%

Melting Point

38° C. (white crystal)

Elementary Analysis Values as $C_{57}H_{92}O_2$: Calculated: C = 84.62%, H = 11.39% Found: C = 84.59%, H = 11.46%

(b) Various Spectral Observations:

Mass spectrum: $M^+$ 808
Infrared spectrum: $\nu$ C=O 1710 cm$^{-1}$
NMR spectrum: absorption owing to an ethyl group newly appeared.

EXAMPLE 17

1-Ethoxycarbonyl-2,6,10,14,18,22,26,30,34,38,42,46-dodecamethyl-heptatetracontadodecaene-1,5,9,13,17,21,25,29,33,37,41,45

(a) Synthesis

In the same manner as described in (a) of Example 1, 2.9 g of triethyl phosphonoacetate and 7.5 g of 6,10,14,18,22,26,30,34,38,42,46-undecamethyl-heptatetracontaundecaene-5,9,13,17,21,25,29,33,37,41,45-one-2 (ordinarily called farnesylfarnesylfarnesylgeranyl methyl ketone were reacted and treated to obtain the intended compound.

In 6,10,14,18,22,26,30,34,38,42,46-undecamethyl-heptatetracontaundecaene-5,9,13,17,21,25,29,33,37,41,45-one-2 used in the above reaction, the trans-form content was 82% with respect to the double bond at the 5-position nearest the carbonyl group, but all of other linkages were wholly of the trans-form. It was a white crystal having a melting point of 41° C.

In 15 ml of n-hexane was dissolved 7.7 g of the resulting product, and purification was carried out by using a glass column packed with 300 g of silica gel in n-hexane according to absorption chromatography (20% benzene/n-hexane mixed solvent was used as an eluting solvent) to obtain 7.1 g of a pure product of the intended compound.

Yield 87.1%

Melting Point

39° C. (white crystal)

Elementary Analysis Values as $C_{62}H_{100}O_2$: Calculated: C = 84.83%, H = 11.52% Found: C = 84.86%, H = 11.49%

(b) Various Spectral Observations:

Mass spectrum: $M^+$ 876
Infrared spectrum: $\nu$ C=O 1710 cm$^{-1}$
NMR spectrum: absorption owing to an ethyl group newly appeared.

Recipes including one of compounds of the present invention, 1-ethoxycarbonyl-2,6,10,14,18,22,26,30,34,38-decamethyl-nonatriacontadecaene-1,5,9,13,17,21,25,29,33,37 (hereinafter referred to as "ethyl decaprenoate"), will now be described as Examples.

Example (Capsules)

| | |
|---|---|
| Ethyl decaprenoate | 5 g |
| Fine crystalline cellulose | 80 g |
| Corn starch | 20 g |
| Lactose | 22 g |
| Polyvinyl pyrrolidone | 3 g |
| Total | 130 g |

The foregoing components were granulated according to a customary method and filled in 1000 of hard capsules of gelatin. Each capsule contained 5 mg of ethyl decaprenoate.

Example 19 (Powder)

| | |
|---|---|
| Ethyl decaprenoate | 50 g |
| Fine crystalline cellulose | 400 g |
| Corn starch | 550 g |
| Total | 1000 g |

Ethyl decaprenoate was dissolved in acetone and adsorbed in fine crystalline cellulose, followed by drying. The dried product was mixed with corn starch and a powder preparation was formed according to a customary method to obtain a powder containing 5% of ethyl decaprenoate.

Example 20 (Tablet)

| | |
|---|---|
| Ethyl decaprenoate | 5 g |
| Corn starch | 10 g |
| Purified sugar | 20 g |
| Calcium carboxymethyl cellulose | 10 g |
| Fine crystalline cellulose | 40 g |
| Polyvinyl pyrrolidone | 5 g |
| Talc | 10 g |
| Total | 100 g |

Ethyl decaprenoate was dissolved in acetone and adsorbed in fine crystalline cellulose, followed by drying. The dried product was mixed with corn starch, purified sugar and calcium carboxymethyl cellulose. An aqueous solution of polyvinyl pyrrolidone was added as a binder to the mixture and granulation was carried out according to a customary method. Then, talc was added as a lubricant to the granules, and the granules were formed into tablets, each weighing 100 mg and containing 5 mg of ethyl decaprenoate.

Example 21 (Injection)

| | |
|---|---|
| Ethyl decaprenoate | 10 g |
| Nikkol HCO-60 | 37 g |
| Sesame oil | 2 g |

| -continued | |
|---|---|
| Sodium chloride | 9 g |
| Propylene glycol | 40 g |
| Phosphoric acid buffer solution (0.1 M, pH of 6.0) | 100 ml |
| Distilled water | balance |
| Total | 1000 ml |

Ethyl decaprenoate was mixed was mixed with Nikkol HCO-60 sesame oil and ½ of propylene glycol and the mixture was heated at about 80° C. to form a solution. Then, a solution of a phosphoric acid buffer solution, sodium chloride and the remainder of propylene glycol in distilled water heated at about 80° C. was added to the above solution to form 1000 ml of an aqueous solution. The aqueous solution was filled in ampoules having a capacity of 2 ml. The ampoules were heat-sealed and sterilized under heating. Each ampoule contained 20 mg.

What we claim is:

1. A method for treating hypertension which comprises administering to a warm-blooded hypertensive subject, a therapeutically effective amount of a polyprenyl carboxylic acid compound having the formula:

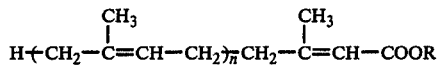

wherein R is selected from the group consisting of hydrogen, alkyl having 1 to 5 carbon atoms, alkenyl having 1 to 5 carbon atoms, cycloalkyl and aryl, and n is an integer of 6 to 11, together with a pharmaceutical carrier.

2. A method as claimed in claim 1 in which R is alkyl having from 1 to 5 carbon atoms.

3. A method as claimed in claim 1 in which R is alkenyl having from 1 to 5 carbon atoms.

4. A method as claimed in claim 1 in which R is cyclohexyl.

5. A method as claimed in claim 1 in which R is phenyl.

6. A method as claimed in claim 1 in which n is 9 and R is selected from the group consisting of ethyl, methyl, t-butyl, cyclohexyl, n-butyl, vinyl and phenyl.

7. A method as claimed in claim 1 in which n is 9 and R is ethyl.

8. A method as claimed in claim 1, wherein the amount of said polyprenyl carboxylic acid compound administered is 10 to 200 mg per day.

9. A method as claimed in claim 1, wherein said polyprenyl carboxylic acid compound is orally administered.

10. A method as claimed in claim 1, wherein said polyprenyl carboxylic acid compound is administered by injection.

* * * * *